United States Patent [19]

Sedelmeier

[11] Patent Number: 4,587,048

[45] Date of Patent: May 6, 1986

[54] PROCESS FOR THE MANUFACTURE OF 4-THIOAZETIDINONE COMPOUNDS

[75] Inventor: Gottfried Sedelmeier, Ehrenkirchen-Norsingen, Fed. Rep. of Germany

[73] Assignee: Ciba-Geigy Corporation, Ardsley, N.Y.

[21] Appl. No.: 601,747

[22] Filed: Apr. 20, 1984

Related U.S. Application Data

[63] Continuation of Ser. No. 375,608, May 6, 1982, abandoned.

[30] Foreign Application Priority Data

May 19, 1981 [CH] Switzerland ............ 3245/81

[51] Int. Cl.$^4$ ............ C07D 205/08; C07D 401/06; C07D 403/06; C07D 401/12
[52] U.S. Cl. ............ 260/239 A; 260/245.4; 260/330.3; 260/330.9; 544/54; 544/58.5; 544/111; 544/335; 544/359
[58] Field of Search ............ 260/239 A, 245.4, 330.3, 260/330.9; 544/359, 111, 54, 335, 58.5

[56] References Cited

U.S. PATENT DOCUMENTS

| | | | |
|---|---|---|---|
| 4,009,159 | 2/1977 | Kamiya ............ | 260/245.4 |
| 4,024,152 | 5/1977 | Kulkolja ............ | 260/245.4 |
| 4,035,362 | 7/1977 | Masai et al. ............ | 260/239 A |
| 4,058,521 | 11/1977 | Uyeo ............ | 260/245.4 |
| 4,066,641 | 1/1978 | Hamashima et al. ............ | 544/17 |
| 4,091,210 | 5/1978 | Kamiya et al. ............ | 260/239 A |
| 4,160,085 | 7/1979 | Tsuji et al. ............ | 544/16 |
| 4,255,328 | 3/1981 | Woodward et al. ............ | 260/239 |
| 4,267,340 | 5/1981 | Kamiya et al. ............ | 548/187 |
| 4,271,296 | 6/1981 | Tsuji ............ | 260/245.4 |
| 4,293,462 | 10/1981 | Woodward et al. ............ | 260/239 |
| 4,319,027 | 3/1982 | Woodward ............ | 260/239 A |
| 4,332,722 | 6/1982 | Tsuji ............ | 260/245.4 |

FOREIGN PATENT DOCUMENTS

| | | | |
|---|---|---|---|
| 1071213 | 2/1980 | Canada ............ | 260/245.4 |
| 65488 | 11/1982 | European Pat. Off. . | |

OTHER PUBLICATIONS

Kamiya et al. I, Chem. Abs. 80, 82619x (1973).
Busson et al., J. Organic Chem. 43, 4434 (1978).
Lecher et al., Chem. Ber. 59, 2594 (1926).
Oae I, J.C.S. Chem. Comm. 1977, 407.
March, "Advanced Organic Chemistry", 2nd Edition, pp. 372–373, 578–581.
Cooper et al., J.A.C.S. 92, 2575 (1970).
Dininno, J.A.C.S. 100, 3251 (1978).
Narisada, Tetrahedron Letters, 1978, p. 1755.
Oae II, JCS Perkins I, 1978, p. 913.
Oae III, Chem. Abs. 90, 87011j (1978).
Oae IV, Chem. Abs. 90, 87002g (1978).
Oae V, Chem. Abs. 90, 121191e (1978).

*Primary Examiner*—Mark L. Berch
*Attorney, Agent, or Firm*—Michael W. Glynn; Irving N. Feit; Irving M. Fishman

[57] ABSTRACT

The present invention relates to a novel process for the manufacture of 4-thioazetidinone compounds of the formula

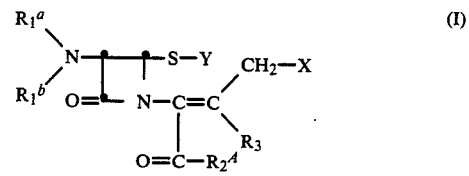

in which $R_1^a$ represents an amino-protecting group and $R_1^b$ represents hydrogen or an acyl radical Ac, or in which $R_1^a$ and $R_1^b$ together represent a bivalent acyl radical, $R_2^A$ represents an etherified hydroxy group, $R_3$ represents methyl, hydroxy, etherified or esterified hydroxy, cyano, tertiary amino or nitro, X represents hydrogen or halogen, and Y represents a group —$SR_4$ or —$SO_2$—$R_5$ in which $R_4$ represents an optionally substituted heteroaryl radical or the acyl radical of an organic carboxylic or thiocarboxylic acid and $R_5$ represents an optionally substituted hydrocarbon radical, or, when $R_3$ represents hydroxy or methyl, tautomers thereof. Compounds of the formula I are manufactured by reacting compounds of the formula III with a nitrosating agent and a compound of the formula IV. Antibiotically active 3-cephem acid derivatives can be manufactured from the compounds of the formula I. The invention relates also to the novel intermediates of the formula III.

21 Claims, No Drawings

PROCESS FOR THE MANUFACTURE OF 4-THIOAZETIDINONE COMPOUNDS

This is a continuation of application Ser. No. 375,608, filed May 6, 1982, now abandoned.

The invention relates to a novel process for the manufacture of 4-thioazetidinone compounds that can be used as starting materials for the manufacture of antibiotically active 3-cephem acid derivatives. The invention relates also to novel intermediates.

The manufacture of 4-thioazetidinones by the reaction of penicillanic acid 1-oxides with mercaptans and optional subsequent reaction with heavy metal sulphinates, especially silver sulphinates, has already been described in German Offenlegungsschrift No. 2 506 330.

In the present invention, an alternative process is proposed for the manufacture of these synthetically valuable compounds from readily available starting materials. The advantage of the novel process resides in the fact that the desired azetidinones can be obtained in high yields, the use of expensive silver salts can be dispensed with and the process according to the invention is suited to being carried out as a "one-pot" process.

The invention relates to a process for the manufacture of 4-thioazetidinone compounds of the formula

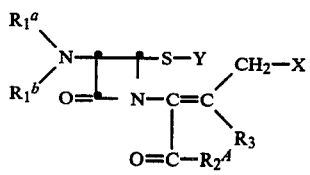
(I)

in which $R_1{}^a$ represents an amino-protecting group and $R_1{}^b$ represents hydrogen or an acyl radical Ac, or in which $R_1{}^a$ and $R_1{}^b$ together represent a bivalent acyl radical, $R_2{}^A$ represents an etherified hydroxy group, $R_3$ represents methyl, hydroxy, etherified or esterified hydroxy, cyano, tertiary amino or nitro, X represents hydrogen or halogen, and Y represents a group $-SR_4$ or $-SO_2-R_5$ in which $R_4$ represents an optionally substituted heteroaryl radical or the acyl radical of an organic carboxylic or thiocarboxylic acid and $R_5$ represents an optionally substituted hydrocarbon radical, or, when $R_3$ represents hydroxy or methyl, tautomers thereof, characterised in that a compound of the formula

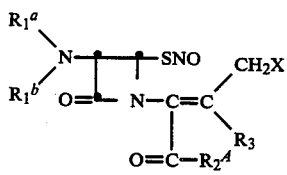
(III)

or, when $R_3$ represents hydroxy or methyl, a tautomer thereof, is treated with a nitrosating agent and a compound of the formula H-Y (IV).

When $R_3$ represents hydroxy or methyl, the compounds of the present invention can alternatively be in the form of tautomers. In such tautomers, the double bond in the substituent attached to the azetidinone nitrogen atom is arranged in the $\beta,\gamma$-position with respect to the carbonyl group of the radical $-C(=O)-R_2{}^A$, in the form

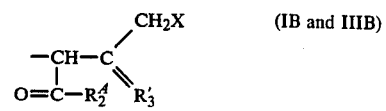
(IB and IIIB)

($R_3{}'$: oxo or methylene). The compounds of the present invention can, however, also be in the form of a mixture of the two isomers.

In the following description of the invention, the term "lower" in groups such as lower alkyl, lower alkylene, lower alkoxy, lower alkanoyl and the like, means that the corresponding groups, unless expressly defined otherwise, contain up to 7, but preferably up to 4, carbon atoms.

In the compounds of the formulae (I) and (II), the symbols $R_1{}^a$, $R_1{}^b$, $R_2{}^A$, $R_3$, X and Y and $R_4$ and $R_5$ have, for example, the following meanings:

An amino-protecting group $R_1{}^a$ is a group that can be replaced by hydrogen, especially an acyl group Ac, also a triarylmethyl group.

An acyl group Ac is especially the acyl radical of an organic acid, preferably having up to 18, and especially up to 10, carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid.

Such an acyl group is especially a radical of the formula

(IA)

in which (1) $R_a$ represents an optionally substituted carbocyclic aryl radical, for example corresponding phenyl, an optionally substituted, preferably unsaturated, cycloaliphatic hydrocarbon radical, for example corresponding cyclohexadienyl or cyclohexenyl, or an optionally substituted heterocyclic aryl radical, for example corresponding thienyl, furyl or thiazolyl, $R_b$ represents hydrogen and $R_c$ represents hydrogen, protected amino or optionally protected hydroxy, carboxyl or sulpho, or in which (2) $R_a$ represents protected $\omega$-amino-$\omega$-carboxy-lower alkyl, for example protected 3-amino-3-carboxypropyl, cyano, etherified hydroxy or mercapto, such as optionally substituted phenoxy, also phenylthio or pyridylthio, or an optionally substituted unsaturated heterocyclic radical bonded via a ring nitrogen atom, for example corresponding tetrazolyl, and $R_b$ and $R_c$ represent hydrogen, or in which (3) $R_a$ represents an optionally substituted carbocyclic aryl radical, for example corresponding phenyl, or an optionally substituted heterocyclic aryl radical, for example corresponding thienyl, furyl or thiazolyl, and $R_b$ and $R_c$ together preferably represent O-substituted hydroxyimino.

Cyclohexadienyl is especially 1,4-cyclohexadienyl, while cyclohexenyl is especially 1-cyclohexenyl.

Thienyl is preferably 2-thienyl, also 3-thienyl, furyl represents especially 2-furyl, thiazolyl is especially 4-thiazolyl, while pyridylthio is, for example, 4-pyridylthio, and tetrazolyl is, for example, 1-tetrazolyl.

Substituents of a phenyl or phenoxy group $R_a$ may be present in any position and are, inter alia, aliphatic hydrocarbon radicals, such as optionally substituted lower alkyl, for example substituted aminomethyl, optionally functionally modified, such as etherified or esterified, hydroxy, substituted amino, or nitro, which, for example, can be, in the 2- or 4-position in the phenoxy group.

Substituents of a cyclohexadienyl or cyclohexenyl group and of a thienyl or furyl group $R_a$ are, for example, optionally substituted lower alkyl, such as substituted aminomethyl, such a substituent being especially in the 2-position of a 1,4-cyclohexadienyl or 1-cyclohexenyl radical or in the 5-position of a 2-thienyl or 2-furyl radical. Substituted thiazolyl is especially 2-amino-4-thiazolyl in which the amino group is protected and/or is substituted by lower alkyl.

Lower alkyl is, for example, methyl, ethyl, propyl, isopropyl, butyl or tert-butyl. Substituted aminomethyl is especially aminomethyl that is protected and optionally additionally substituted by lower alkyl, for example protected methylaminomethyl, while etherified hydroxy can be, for example, lower alkoxy, such as methoxy or ethoxy, and esterified hydroxy can be, for example, lower alkanoyloxy, such as acetoxy or pivaloyloxy, aroyloxy, for example benzoyloxy, carbamoyloxy or halogen, for example chlorine or bromine, and substituted amino can be, for example, amino that is protected and optionally additionally substituted by lower alkyl, for example protected methylamino, or lower alkylsulphonylamino, for example methylsulphonylamino.

O-substituted hydroxyimino is especially lower alkoxyimino, for example methoxyimino or ethoxyimino, also phenoxyimino or phenyl-lower alkoxyimino, for example benzyloxyimino, such groups being preferably in the syn-form.

A triarylmethyl group $R_1^a$ is especially a triphenylmethyl group.

A bivalent acyl radical formed by the radicals $R_1^a$ and $R_1^b$ together is, for example, the diacyl radical of an organic dicarboxylic acid, preferably having up to 18 carbon atoms, especially of an aliphatic or aromatic dicarboxylic acid, for example the acyl radical of a lower alkane- or lower alkenedicarboxylic acid, such as succinyl, or of an o-arylenedicarboxylic acid, such as phthaloyl. There also comes into consideration the acyl radical of an α-aminoacetic acid that is preferably substituted in the α-position, for example contains an aromatic or heterocyclic radical, and in which the amino group is bonded to the nitrogen atom via a preferably substituted methylene radical, for example a methylene radical containing 2 lower alkyl groups, such as methyl groups, for example a 1-oxo-3-aza-1,4-butylene radical that is substituted especially in the 2-position, for example contains optionally substituted phenyl or thienyl and that is optionally mono- or di-substituted in the 4-position by lower alkyl, such as methyl, for example 4,4-dimethyl-2-phenyl-1-oxo-3-aza-1,4-butylene.

Preferably, $R_1^a$ represents phenylacetyl or phenoxyacetyl and $R_1^b$ represents hydrogen.

Etherified hydroxy groups $R_2^A$ are hydroxy groups etherified by aliphatic, cycloaliphatic, cycloaliphatic-aliphatic, aromatic or araliphatic radicals, especially optionally substituted hydrocarbon radicals of this type, and also heterocyclic or heterocyclic-aliphatic radicals having preferably up to 18 carbon atoms. Such a group is, for example, 2-halo-lower alkoxy in which halogen preferably has an atomic weight of over 19, for example 2,2,2-trichloroethoxy or 2-iodoethoxy, also 2-chloroethoxy or 2-bromoethoxy which can be readily converted into the latter, or 2-lower alkylsulphonyl-lower alkoxy, for example 2-methylsulphonylethoxy. The group $R_2^A$ is also a methoxy group poly-substituted by optionally substituted hydrocarbon radicals, especially saturated aliphatic or aromatic hydrocarbon radicals, such as lower alkyl, for example methyl, and/or phenyl, or a methoxy group mono-substituted by an unsaturated aliphatic hydrocarbon radical, such as lower alkenyl, for example vinyl or allyl, by a carbocyclic aryl group having electron-donating substituents, or by a heterocyclic group of aromatic character having oxygen or sulphur as ring member, such as tert-lower alkoxy, for example tert-butoxy or tert-pentyloxy, optionally substituted diphenylmethoxy, for example diphenylmethoxy or 4,4'-dimethoxydiphenylmethoxy, lower alkenyloxy, especially 2-lower alkenyloxy, for example allyloxy, lower alkoxyphenyl-lower alkoxy, for example lower alkoxybenzyloxy, such as methoxybenzyloxy (methoxy being especially in the 3-, 4- and/or 5-position), especially 3- or 4-methoxybenzyloxy or 3,4-dimethoxybenzyloxy, or most especially nitrobenzyloxy, for example 2- or 4-nitrobenzyloxy, or 4,5-dimethoxy-2-nitrobenzyloxy, or fufuryloxy, such as 2-furfuryloxy. $R_2^A$ can alternatively be 2-oxo- or 2-thiacycloalkoxy or -cycloalkenyloxy having from 5 to 7 ring members, such as 2-tetrahydrofuryloxy, 2-tetrahydropyranyloxy or 2,3-dihydro-2-pyranyloxy, or arylcarbonylmethoxy, in which aryl is especially an optionally substituted phenyl group, for example phenacyloxy, or optionally substituted phenoxy, for example nitrophenoxy, for example 4-nitrophenoxy or 2,4-dinitrophenoxy, or polyhalophenoxy, for example pentachlorophenoxy. $R_2^A$ can, however, also represent unbranched lower alkoxy, for example methoxy or ethoxy.

In radicals $R_3$, etherified hydroxy is especially lower alkoxy, for example methoxy or ethoxy, or aryl-lower alkoxy, for example benzyloxy. Esterified hydroxy is especially hydroxy esterified by lower alkanecarboxylic acids, organic sulphonic acids, nitrous acid, phosphinic or phosphoric acids or hydrohalic acids, and represents, for example, lower alkanoyloxy, for example formyloxy or acetoxy, sulphonyloxy, such as methanesulphonyloxy or optionally substituted benzenesulphonyloxy, especially p-bromo- or p-toluene-sulphonyloxy, nitrito, phosphinoyloxy, for example diphenylphosphinoyloxy, phosphoryloxy, for example diethoxyphosphoryloxy, or halogen, for example chlorine or bromine.

Tertiary amino $R_3$ is, for example, a group of the formula $-N(R_3^a)(R_3^b)$. Suitable substituents $R_3^a$ and $R_3^b$, which can be the same or different, are especially aliphatic and cycloaliphatic hydrocarbon radicals that contain, for example, up to 18, especially up to 12 and preferably up to 7, carbon atoms. Aliphatic hydrocarbon radicals are, for example, lower alkyl groups that are optionally substituted, for example by lower alkoxy, such as methoxy, lower alkylthio, such as methylthio, cycloalkyl, such as cyclohexyl, aryl, such as phenyl, or by heteroaryl, such as thienyl, for example methyl, ethyl, propyl, isopropyl, butyl, isobutyl, pentyl, hexyl, 2-ethoxyethyl, 2-methylthioethyl, cyclohexylmethyl, benzyl or thienylmethyl. Cycloaliphatic hydrocarbon radicals are, for example, cycloalkyl groups that are optionally substituted, for example by lower alkyl, such as methyl, lower alkoxy, such as methoxy, lower alkylthio, such as methylthio, cycloalkyl, such as cyclohexyl, aryl, such as phenyl, or by heteroaryl, such as furyl, such as optionally substituted, for example as indicated, cyclopropyl, cyclopentyl, cyclohexyl or cycloheptyl.

$R_3{}^a$ and $R_3{}^b$ can also together represent lower alkylene, for example 1,4-butylene or 1,5-pentylene, or lower alkylene interrupted by oxygen, sulphur or optionally lower alkylated, for example methylated, nitrogen, for example 3-aza-, 3-methyl-3-aza- or 3-oxa-pentylene. Suitable tertiary amino groups —N($R_3{}^a$)($R_3{}^b$) are, for example, dimethylamino, diethylamino, dicyclohexylamino, pyrrolidin-1-yl, morpholin-4-yl or 4-methylpiperazin-1-yl.

$R_3$ represents especially hydroxy, methyl, methoxy, acetoxy, methanesulphonyloxy, nitrito, pyrrolidin-1-yl or morpholin-1-yl.

X as halogen is especially chlorine or bromine.

In a group —$SR_4$, $R_4$ is, for example, an optionally substituted heteroaryl radical having up to 15, but preferably up to 9, carbon atoms and at least one ring nitrogen atom and optionally a further ring hetero atom, such as an oxygen or sulphur atom, which radical is bonded by one of its ring carbon atoms to the thio group —S—. Radicals $R_4$ are monocyclic or bicyclic and can be substituted, for example, by lower alkyl, such as methyl or ethyl, lower alkoxy, such as methoxy or ethoxy, halogen, such as fluorine, chlorine or bromine, or by aryl, such as phenyl.

Radicals $R_4$ are, for example, five-membered heteroaryl radicals, such as thiadiazolyl, thiatriazolyl, oxadiazolyl or oxatriazolyl, but especially diazolyl, oxazolyl and thiazolyl and primarily the corresponding benzo derivatives, such as benzdiazolyl, benzoxazolyl or benzthiazolyl, wherein a substitutable ring nitrogen atom may be substituted, for example, by lower alkyl, such as methyl. Six-membered heteroaryl radicals, such as quinolyl, are also suitable. Representative of such groups $R_4$ are, for example, 1-methylimidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 1-methylbenzimidazol-2-yl, benzoxazol-2-yl and especially benzthiazol-2-yl, also quinolyl.

Further groups $R_4$ are acyl radicals of organic carboxylic or thiocarboxylic acids, such as optionally substituted aliphatic, cycloaliphatic, araliphatic or aromatic acyl or thioacyl groups having up to 18, but preferably up to 10, carbon atoms, such as lower alkanoyl, for example acetyl or propionyl, lower thioalkanoyl, for example thioacetyl or thiopropionyl, cycloalkanoyl, for example cyclohexanoyl, cycloalkanethiocarbonyl, for example cyclohexanethiocarbonyl, benzoyl, thiobenzoyl, naphthoyl, naphthylthiocarbonyl, heterocyclic carbonyl or thiocarbonyl, such as 2-, 3- or 4-pyridylcarbonyl, 2- or 3-thenoyl, 2- or 3-furoyl, 2-, 3- or 4-pyridylthiocarbonyl, 2- or 3-thiothenoyl, 2- or 3-thiofuroyl, or corresponding acyl or thioacyl groups that are mono- or poly-substituted, for example by lower alkyl, such as methyl, halogen, such as fluorine or chlorine, lower alkoxy, such as methoxy, aryl, such as phenyl, or by aryloxy, such as phenoxy.

An optionally substituted hydrocarbon radical $R_5$ in groups —$SO_2$—$R_5$ is especially a corresponding aliphatic, cycloaliphatic, araliphatic or aromatic hydrocarbon radical having up to 18, but preferably up to 10, carbon atoms. Suitable radicals $R_5$ are, for example, optionally substituted alkyl groups, especially lower alkyl groups, such as methyl, ethyl or butyl groups, alkenyl groups, for example allyl or butenyl groups, cycloalkyl groups, for example cyclopentyl or cyclohexyl groups, such as the above groups mono- or poly-substituted by lower alkoxy, for example methoxy, halogen, for example fluorine, chlorine or bromine, aryl, for example phenyl, or by aryloxy, for example phenoxy, or are naphthyl or especially phenyl groups optionally mono- or poly-substituted by lower alkyl, for example methyl, lower alkoxy, for example methoxy, halogen, for example fluorine, chlorine or bromine, aryl, for example phenyl, aryloxy, for example phenoxy, or by nitro, for example phenyl, 2-, 3- or, preferably, 4-tolyl, 2-, 3- or, preferably, 4-methoxyphenyl, 2-, 3- or 4-chlorophenyl, 4-biphenylyl, 4-phenoxyphenyl, 4-nitrophenyl or 1 or 2-naphthyl.

Preferred radicals $R_4$ are, for example, 1,3-oxazol-2-yl, 1,3-thiazol-2-yl, benzoxazol-2-yl and especially benzthiazol-2-yl. Preferred radicals $R_5$ are, for example, unsubstituted phenyl or phenyl substituted by methyl, methoxy, bromine or nitro, especially p-tolyl.

Protected hydroxy, amino, carboxyl or sulpho groups in acyl radicals of the formula (IA) are those that are customary in penicillin and cephalosporin chemistry and that can be readily converted into free hydroxy, amino, carboxyl or sulpho groups without the molecular framework being destroyed or other undesired side reactions taking place.

Protecting groups of this type and their removal are described, for example, in "Protective Groups in Organic Chemistry", Plenum Press, London, New York, 1973, in "The Peptides", Vol. I, Schröder and Lübke, Academic Press, London, New York, 1965, and in Houben-Weyl, "Methoden der organischen Chemie", 4th edition, Vol. 15/1, Georg Thieme Verlag, Stuttgart, 1974.

Amino groups may be protected, for example by acyl radicals, an acyl radical being especially an acyl radical of a semiester of carbonic acid that can be removed by reduction, for example by treatment with a chemical reducing agent or with catalytically activated hydrogen, or by solvolysis, for example by treatment with a suitable acid, and also by irradiation, such as a lower alkoxycarbonyl radical that is branched several times preferably at the first carbon atom of the esterifying group and/or that is substituted by aryl, for example phenyl or biphenylyl that is optionally substituted, for example by lower alkoxy, for example methoxy, and/or nitro, or by arylcarbonyl, especially benzoyl: for example tert-butoxycarbonyl, tert-pentyloxycarbonyl, diphenylmethoxycarbonyl, 2-(4-biphenylyl)-2-propoxycarbonyl, benzyloxycarbonyl, 4-nitrobenzyloxycarbonyl, 2-nitro-4,5-dimethoxybenzyloxycarbonyl or phenacyloxycarbonyl, or a lower alkoxycarbonyl radical substituted at the second carbon atom of the esterifying group by halogen, for example 2,2,2-trichloroethoxycarbonyl or 2-iodoethoxycarbonyl, also polycyclic cycloalkoxycarbonyl, for example adamantyloxycarbonyl.

An amino group may also be protected by an arylmethyl radical, such as a polyarylmethyl radical, for example by trityl, a 2-carbonylvinyl grouping, such as a 1-lower alkoxycarbonyl-1-propen-2-yl group, for example 1-methoxycarbonyl-1-propen-2-yl, an arylthio or aryl-lower alkylthio group, for example 2-nitrophenylthio or pentachlorophenylthio, also tritylthio, a phosphinoyl group, for example diphenylphosphinoyl, or a sulphonyl group, such as a lower alkanesulphonyl group, for example methanesulphonyl, or an arenesulphonyl group, for example a p-toluenesulphonyl group.

Hydroxy-protecting groups are, for example, acyl radicals, especially one of the acyl radicals of carbonic acid semiesters mentioned in connection with a protected amino group, also readily removable 2-oxa- or 2-thiaaliphatic or -cycloaliphatic hydrocarbon radicals, especially 1-lower alkoxy-lower alkyl or 1-lower alkylthio-lower alkyl, for example 1-methoxyethyl, 1-ethoxyethyl, 1-methylthioethyl or 1-ethylthioethyl, or 2-oxa- or 2-thia-cyclo-lower alkyl having from 5 to 7 ring atoms, for example 2-tetrahydrofuryl or 2-tetrahydropyranyl, or the corresponding thia analogues, and also readily removable optionally substituted α-phenyl-lower alkyl radicals, such as optionally substituted benzyl or diphenylmethyl, there being suitable as substituents of the phenyl radicals, for example, halogen, such as chlorine, lower alkoxy, such as methoxy, and/or nitro.

A protected carboxyl or sulpho group is especially a carboxyl or sulpho group esterified by an aliphatic, cycloaliphatic, cycloaliphatic-aliphatic, aromatic or araliphatic alcohol, such as a lower alkanol. In a carboxyl or sulpho group the hydroxy group may be esterified, for example by an alcohol of the formula $R_2^A$-H.

The invention relates especially to a process for the manufacture, from correspondingly substituted compounds of the formula III, of compounds of the formula I in which $R_1^a$ represents an acyl group of the formula IA in which (1) $R_a$ represents phenyl that is optionally substituted by hydroxy, protected hydroxy, lower alkyl, lower alkoxy, lower alkanoyloxy, aroyloxy, halogen, lower alkylsulphonylamino, nitro or by substituted aminomethyl; or thienyl, furyl, cyclohexadienyl or cyclohexenyl each of which is substituted by lower alkyl or substituted aminomethyl; or thiazolyl substituted by di-lower alkylamino or protected amino, $R_b$ represents hydrogen and $R_c$ represents hydrogen, optionally protected hydroxy, protected amino, protected carboxyl or protected sulpho, or in which (2) $R_a$ represents protected 3-amino-3-carboxypropyl; cyano; 1-tetrazolyl; phenoxy that is optionally substituted by hydroxy, protected hydroxy, lower alkyl, lower alkoxy, lower alkanoyloxy, aroyloxy, halogen, lower alkylsulphonylamino, nitro or by substituted aminomethyl; or pyridylthio, and $R_b$ and $R_c$ represent hydrogen, or in which (3) $R_a$ represents phenyl that is optionally substituted by hydroxy, protected hydroxy, lower alkyl, lower alkoxy, lower alkanoyloxy, aroyloxy, halogen, lower alkylsulphonylamino, nitro or by substituted aminomethyl; or thienyl or furyl each of which is substituted by lower alkyl or substituted aminomethyl; or thiazolyl substituted by di-lower alkylamino or protected amino, and $R_b$ and $R_c$ together represent syn-lower alkoxyimino, and $R_1^b$ represents hydrogen, $R_2^A$ represents lower alkoxy; 2-halo-lower alkoxy; 2-lower alkenyloxy; methoxy mono- or di-substituted by phenyl that is optionally substituted by lower alkoxy and/or nitro; trityloxy; or phenoxy that is optionally substituted by nitro or halogen, $R_3$ is methyl, hydroxy, lower alkoxy, phenyl-lower alkoxy, lower alkanoyloxy, sulphonyloxy, nitrito, phosphinoyloxy, phosphoryloxy, halogen, cyano, nitro, or amino that is di-substituted by lower alkyl, lower alkoxy-lower alkyl or cycloalkyl or that has as substituent lower alkylene interrupted by oxygen, sulphur or optionally lower alkylated nitrogen, X represents hydrogen or halogen and Y represents a radical —SR$_4$ or —SO$_2$—R$_5$ in which R$_4$ represents thiadiazolyl, oxathiazolyl, diazolyl, oxazolyl, thiazolyl, benzthiazolyl, benzoxazolyl or benzthiazolyl, each of which is optionally substituted by lower alkyl, and R$_5$ represents lower alkyl; cycloalkyl; or phenyl or naphthyl each of which is optionally substituted by lower alkyl, lower alkoxy, halogen, phenyl, phenoxy, or by nitro, or, when R$_3$ is hydroxy or methyl, tautomers thereof.

The invention relates preferably to a process for the manufacture, from correspondingly substituted compounds of the formula III, of compounds of the formula I in which $R_1^a$ represents an acyl group of the formula IA in which $R_a$ represents phenyl or phenoxy each of which is unsubstituted or substituted by protected hydroxy, for example tert-butoxycarbonyloxy or 2-tetrahydropyranyloxy, lower alkoxy, for example methoxy, or by protected aminomethyl, for example tert-butoxycarbonylaminomethyl; or thienyl, for example 2-thienyl; furyl, for example 2-furyl; cyclohexadienyl, for example 1,4-cyclohexadienyl; or protected 3-amino-3-carboxypropyl, for example 3-benzoylamino-3-diphenylmethoxycarbonylpropyl, and $R_b$ and $R_c$ represent hydrogen, and $R_1^b$ represents hydrogen, $R_2^A$ represents lower alkoxy, for example methoxy or tert-butoxy; 2-halo-lower alkoxy, for example 2-iodo- or 2,2,2-trichloro-ethoxy; 2-lower alkenyloxy, for example allyloxy; benzyloxy that is unsubstituted or substituted in the 4-position by nitro; diphenylmethoxy that is unsubstituted or disubstituted in the 4- and 4'-position by methoxy; or trityloxy, $R_3$ represents methyl, lower alkoxy, for example methoxy, phenyl-lower alkoxy, for example benzyloxy, hydroxy, sulphonyloxy, for example methane- or p-toluenesulphonyloxy, nitrito, phosphinoyloxy, for example diphenylphosphinoyloxy, phosphoryloxy, for example diethoxyphosphoryloxy, halogen, for example bromine, cyano, nitro, di-lower alkylamino, for example dimethylamino, dicycloalkylamino, for example dicyclohexylamino, pyrrolidin-1-yl, morpholin-4-yl or 4-methylpiperazin-1-yl, X represents hydrogen or halogen, for example bromine, and Y represents heteroarylthio, such as oxazolyl-, for example 1,3-oxazol-2-yl-, thiazolyl-, for example 1,3-thiazol-2-yl-, benzoxazol-2-yl- or benzthiazol-2-yl-thio, or benzenesulphonyl that is unsubstituted or substituted by lower alkyl, for example methyl, lower alkoxy, for example methoxy, halogen, for example bromine, or by nitro, or, when $R_3$ represents hydroxy or methyl, tautomers thereof.

The invention relates especially to a process for the manufacture, from correspondingly substituted compounds of the formula III, of 3-amino-4-thioazetidin-2-ones of the formula I in which $R_1^a$ represents an acetyl radical of the formula IA in which $R_a$ represents phenyl, thienyl, for example 2-thienyl, or phenoxy, and $R_b$ and $R_c$ represent hydrogen, $R_1^b$ represents hydrogen, $R_2^A$ represents lower alkoxy, for example tert-butoxy, 2-halo-lower alkoxy, for example 2,2,2-trichloroethoxy, benzyloxy optionally substituted in the 4-position by nitro, or diphenylmethoxy, X represents hydrogen or halogen, for example bromine, $R_3$ represents methyl, hydroxy, lower alkoxy, for example methoxy, sulphonyloxy, for example methanesulphonyloxy, nitrito, di-lower alkylamino, for example dimethylamino, pyrrolidin-1-yl or morpholin-1-yl, and Y represents bicyclic heteroarylthio, for example benzthiazol-2-ylthio, or benzenesulphonyl that is unsubstituted or substituted in the 4-position by lower alkyl, for example methyl, or, when $R_3$ represents hydroxy or methyl, tautomers thereof.

Inorganic or organic nitrosating agents can be used for the process according to the invention. Inorganic nitrosating agents are, for example, nitrous acid and anhydrides thereof, for example the symmetric anhydride dinitrogen trioxide, also dinitrogen tetroxide and mixed anhydrides with hydrohalic acids, such as nitrosyl chloride or bromide, also nitrosyl tetrafluoroborate and nitrosylsulphuric acid. Suitable as organic nitrosating agents are especially lower alkyl esters of nitrous acid, the lower alkyl radical being especially ethyl, isopropyl, n-butyl, n-pentyl or isopentyl (isoamyl).

Suitable compounds of the formula IV are, for example, mercaptans of the formula R$_4$—SH (IVa) and sulphinic acids of the formula R$_5$—SO$_2$H (IVb) in which R$_4$ and R$_5$ have the meanings indicated.

The reaction of the thionitrites of the formula III with the compounds of the formula IV can be carried out in the presence of at least stoichiometric quantities of one of the mentioned nitrosating agents, such as nitrous acid, dinitrogen trioxide, dinitrogen tetroxide or a lower alkyl nitrite, for example isoamyl nitrite, in an inert solvent, for example in a lower alkanol, for example ethanol, or in a chlorinated hydrocarbon, for example methylene chloride, chloroform or tetrachloroethane, or, when using nitrous acid or a lower alkyl nitrite as the nitrosating agent, alternatively in a two-phase water/organic solvent system, there being suitable as organic solvent especially chlorinated hydrocarbons, for example chloroform, methylene chloride or tetrachloroethane, dilower alkyl ethers, for example diethyl or di-n-butyl ether, or a hydrocarbon, for example decalin. The reaction is carried out in a temperature range of between −70° and +50° C. and preferably at approximately −10° to approximately +40° C.

In a preferred embodiment of the process, thionitrites of the formula III are reacted with compounds of the formula IVa or IVb in the presence of isoamyl nitrite as the nitrosating agent in the system water/chlorohydrocarbon, for example water/methylene chloride, at approximately from 20° to 25° C.

The manufacture of the starting materials of the formula III can be carried out under conditions such that these materials can be isolated from the reaction mixture and purified, for example by chromatographic methods, before they are further processed to form the end products of the formula I. The starting materials of the formula III are, however, preferably manufactured in situ and further reacted to form the end products of the formula I without being isolated from the reaction mixture. The invention relates also to these "one-pot" processes.

The invention therefore relates also to processes for the manufacture of compounds of the formula III

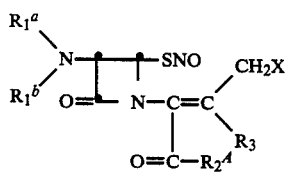 (III)

in which R$_1{}^a$ represents an amino-protecting group and R$_1{}^b$ represents hydrogen or an acyl radical Ac, or in which R$_1{}^a$ and R$_1{}^b$ together represent a bivalent acyl radical, R$_2{}^A$ represents an etherified hydroxy group, R$_3$ represents methyl, hydroxy, etherified or esterified hydroxy, cyano, tertiary amino or nitro, and X represents hydrogen or halogen, or, when R$_3$ represents hydroxy or methyl, tautomers thereof, characterised in that (a) a mercaptoazetidinone of the formula

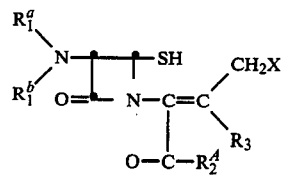 (II)

or a salt thereof, or, when R$_3$ represents hydroxy or methyl, a tautomer thereof, is treated with a nitrosating agent, or (b) for the manufacture of 4-nitrosothioazetidinones of the formula

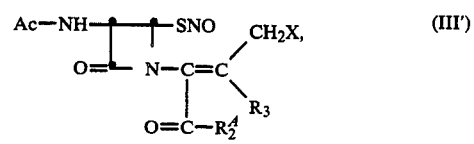 (III′)

in which Ac represents an acyl group, and R$_2{}^A$, R$_3$ and X have the meanings given under formula III, or, when R$_3$ represents hydroxy or methyl, a tautomer thereof, a diazabicycloheptene of the formula

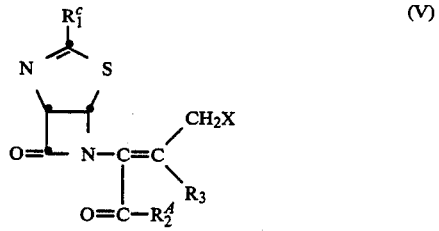 (V)

in which R$_1{}^c$ represents a radical derived from the acyl group Ac but without the carbonyl group, or, when R$_3$ represents hydroxy or methyl, a tautomer thereof, is treated with an acidic hydrolysis agent and a resulting intermediate of the formula

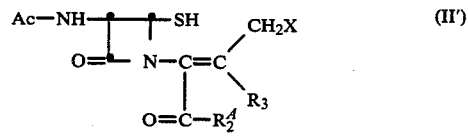 (II′)

or, when R$_3$ represents hydroxy or methyl, a tautomer thereof, is treated with a nitrosating agent, optionally without being isolated from the reaction mixture, or (c) for the manufacture of 4-nitrosothioazetidinones of the formula

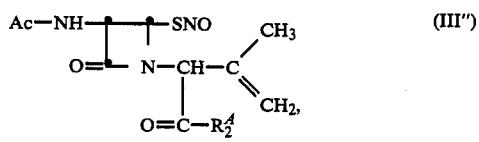 (III″)

a penicillin-1-oxide of the formula

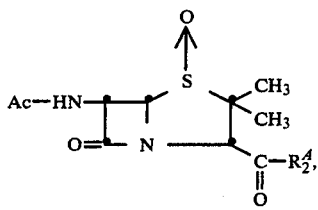

(VI)

in which Ac has the meaning given under formula III' and $R_2^A$ has the meaning given under formula III, is reacted with a compound of trivalent phosphorus, a resulting intermediate of the formula

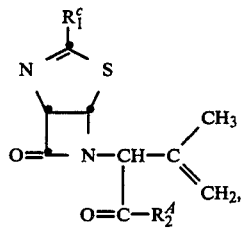

(V')

in which $R_1^c$ has the meaning given under formula V, is treated with an acidic condensation agent, optionally without being isolated from the reaction mixture, and the resulting intermediate of the formula

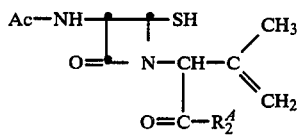

(II'')

is treated with a nitrosating agent, optionally without being isolated from the reaction mixture.

The invention relates especially to the processes mentioned in the Examples for the manufacture of compounds of the formula III.

Process (a)

Salts of compounds of the formula II are, for example, alkali metal salts, for example sodium or potassium salts, alkaline earth metal salts, for example calcium salts, or heavy metal salts, for example silver or mercury salts.

Inorganic or organic nitrosating agents, such as those described above in connection with the manufacture of the end products of the formula I, can be used as nitrosating agents.

The nitrosation of the mercaptans of the formula II is carried out in a solvent that is inert towards the nitrosating agent. When using nitrous acid, which is advantageously produced by the action of a mineral acid, for example hydrochloric or sulphuric acid, a lower alkanoic acid, for example acetic acid, or an acidic salt, for example potassium bisulphate or aluminium sulphate, on an alkali metal nitrite, for example sodium nitrite, or when using an ionic nitrosyl salt, for example nitrosyl tetrafluoroborate, the operation is carried out preferably in aqueous phase, the compounds of the formula II being maintained in suspension by vigorous stirring, or in a two-phase system that contains, in addition to water, a solvent phase for the compound of the formula II, for example a hydrocarbon, for example benzene, decalin or hexane, a chlorinated hydrocarbon, for example methylene chloride, chloroform or tetrachloroethane, a di-lower alkyl ether, for example diethyl or di-n-butyl ether, or an ester, for example ethyl acetate. The nitrosation can, however, alternatively be carried out in homogeneous solution, for example in glacial acetic acid. When using dinitrogen trioxide, nitrosyl halides or lower alkyl nitrites as nitrosating agents, the operation is carried out, as described, in a two-phase solvent system, or in a homogeneous organic phase, for example in one of the mentioned hydrocarbons, chlorinated hydrocarbons or di-lower alkyl ethers, or in a lower alkanol, for example ethanol or n-butanol, in 1,2-dimethoxyethane, diethylene glycol monomethyl ether or in an acid amide, for example dimethylformamide or hexamethylphosphoric acid triamide. The reaction with nitrosyl halides is carried out optionally in the presence of a base, such as an alkali metal carbonate or an alkaline earth metal carbonate, for example sodium, potassium or magnesium carbonate, or preferably in the presence of an organic nitrogen base, for example pyridine, quinoline, dimethylaniline or triethylamine, it being possible for the nitrogen bases mentioned to serve simultaneously as solvents. Salts of compounds of the formula II, for example alkali metal salts, such as sodium salts, can be reacted with nitrosyl halides, it being advantageous to select a solvent in which an inorganic salt being formed, for example an alkali metal halide, is insoluble and precipitates out of the reaction mixture. Suitable are especially the mentioned di-lower alkyl ethers, chlorinated hydrocarbons and benzene. If necessary, the nitrosation is carried out in an inert gas atmosphere, for example a nitrogen atmosphere.

The reaction temperature is between $-70°$ and $+50°$ C. and preferably between $-20°$ and $+40°$ C.

A preferred form is nitrosation with isoamyl nitrite in a two-phase water/halohydrocarbon system, for example a water/methylene chloride system, at approximately from 20° to 25° C.

The thionitrite of the formula III obtainable according to the process can be further reacted to form the end products of the formula I optionally without being isolated from the reaction mixture.

In that case a compound of the formula II is used as the starting material and the nitrosation is carried out, preferably in a water/chlorohydrocarbon phase, for example a water/methylene chloride phase, with at least 2 molar equivalents of a nitrosating agent, for example with isoamyl nitrite, in the presence of a compound of the formula IVa or IVb, the thionitrite of the formula III formed as an intermediate being further reacted in situ to form the end products of the formula I.

The starting materials of the formula II are known or can be manufactured according to methods known per se.

The starting materials of the formula II in which $R_1^b$ represents hydrogen can be manufactured, for example, by subjecting 4-thia-2,6-diazabicyclo[3.2.0]heptenes of the formula

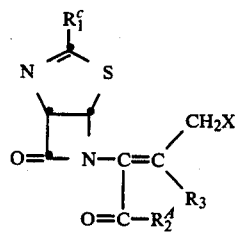

(V)

or tautomers thereof, to acidic hydrolysis, as described in Belgian Patent Specification 838 656 and under process (b) below.

The starting materials of the formula II can also be manufactured by solvolysing an azetidinone of the formula

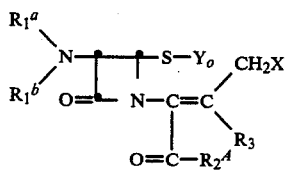

(VII)

in which $Y_o$ represents a solvolytically removable radical, for example the trimethylsilyl group, or, when $R_3$ represents hydroxy or methyl, a tautomer thereof, for example hydrolysing with an aqueous mineral acid, such as hydrochloric acid, or solvolysing with an alcohol, for example methanol. The mentioned compounds of the formula VII can be obtained by treating a mercaptan of the formula VIII (described in German Offenlegungsschrift No. 26 55 298)

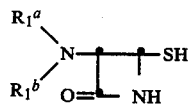

(VIII)

with trimethylsilyl chloride and introducing the radical —C(—COR$_2^A$)=C(R$_3$)(CH$_2$X) or —CH(—COR$_2^A$)—C(=R$_3$')(CH$_2$X) into the resulting compound of the formula IX

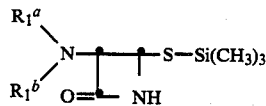

(IX)

by reaction with a compound of the formula X

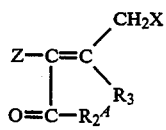

(X)

in which Z represents halogen, for example bromine, or, when $R_3$ represents hydroxy or methyl, with a tautomer thereof. It is, however, also possible to react the compounds of the formula IX with a glyoxylic acid ester of the formula OHC—CO—R$_2^A$, in the resulting adduct of the formula XI

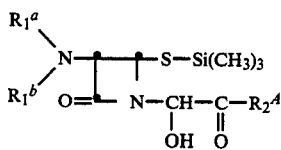

(XI)

to exchange the hydroxy group for bromine using phosphorus tribromide and then to synthesise the radical —C(—COR$_2^A$)=C(R$_3$)(CH$_2$X) or —CH(—COR$_2^A$)—C(=R$_3$')(CH$_2$X) according to the Wittig process.

Process (b)

A radical $R_1{}^c$ derived from the acyl group Ac but without the carbonyl group is especially a radical of the formula —C(R$_a$, R$_b$, R$_c$) in which R$_a$, R$_b$ and R$_c$ have the meanings given above. $R_1{}^c$ is preferably benzyl or phenoxymethyl.

An acidic hydrolysis agent is especially an aqueous acid. There are preferably used inorganic acids, such as hydrohalic acids, for example hydrochloric acid, sulphuric acid, nitric acid, phosphoric acid, tetrafluroboric aicd, perchloric acid or chloric acid, organic sulphonic acids, such as lower alkanesulphonic acid, for example methanesulphonic acid, benzenesulphonic acids optionally substituted by methyl or bromine, for example p-toluenesulphonic acid, aralkylsulphonic acids, for example benzylsulphonic acid, or α-haloalkanesulphonic acids, for example trifluoromethanesulphonic acid, α-halocarboxylic acids, for example trifluoro- or dichloroacetic acid, or polycarboxylic acids, for example oxalic acid.

Process (b) according to the invention is preferably carried out as a "one-pot process". It is, however, also possible to break off the process at the stage of the mercaptan of the formula II', to isolate the product and to use this product in the further reaction steps.

The hydrolysis of the diazabicycloheptenes of the formula V is carried out with an aqueous solution of one of the acids mentioned. The operation is carried out in an organic solvent in which the acid and water dissolve, for example in a lower alkanol, such as ethanol, a lower alkanone, for example acetone, an amide, for example dimethylformamide, a sulphoxide, for example dimethyl sulphoxide, or in excess water, or under two-phase conditions in a solvent in which the starting compound of the formula V dissolves, for example in a halogenated hydrocarbon, such as methylene chloride, an ester, such as ethyl acetate, or an ether, such as diethyl ether, or in mixtures of these solvents. In order to avoid side reactions, such as cleavage of the azetidinone ring, the operation is carried out at a reaction temperature of approximately from 10° to 30° C., but preferably at room temperature.

The further reaction of the resulting mercaptan II' to form the thionitrite of the formula III', or, in the "one-pot process", to form the end products of the formula I in which $R_1{}^a$ represents an acyl radical Ac and $R_1{}^b$ represents hydrogen and $R_2{}^A$, $R_3$ and Y have the meanings given under formula I, is carried out in the same manner as described under process (a). The operation is carried out preferably in one of the two-phase solvent systems indicated with a lower alkyl nitrite or nitrous acid as the nitrosating agent.

In an especially preferred form of the process according to the invention, a solution of a compound of the formula V in a chlorohydrocarbon, for example methylene chloride, is used as the starting material, hydrolysis is carried out, optionally in the presence of a second organic solvent that is water-miscible and can serve as a solubiliser, for example acetone, with a dilute mineral acid, for example hydrochloric or sulphuric acid, or sulphonic acid, for example p-toluenesulphonic acid, and the resulting azetidinone II' is reacted, without being isolated from the reaction mixture, with 2 molar equivalents of a nitrosating agent, for example isoamyl nitrite, in the presence of a mercaptan of the formula IVa or of a sulphinic acid of the formula IVb, the thionitrite III' formed as an intermediate further reacting in situ to form the end products of the formula I.

Process (c)

A compound of trivalent phosporus is preferably a tri-lower alkylphosphite, for example trimethyl or triethyl phosphite, or a triarylphosphine, especially triphenylphosphine.

Process (c) according to the invention is preferably carried out as a "one-pot process". It is, however, also possible to break off the process at any stage, isolate the product and use this product in the further reaction steps.

The conversion of the penicillin-1-oxide of the formula VI into the bicyclic amide of the formula V' is carried out in a solvent that is inert towards the reactants, for example in an aromatic hydrocarbon, for example benzene or toluene, or in a chlorinated hydrocarbon, for example ethylene chloride or carbon tetrachloride. The operation is carried out in the presence of a mild dehydrating agent, for example calcium chloride, silica gel or a molecular sieve, or with the removal by distillation, preferably azeotropic distillation, of the water freed in the reaction. The reaction temperature is at approximately from 70° to 110° C., but preferably at the boiling temperature of the solvent used.

The solution of the bicyclic amide of the formula V', formed optionally after filtering off the dehydrating agent, can be further reacted directly without additional isolation steps. It is, however, also possible to concentrate the solution and to use it further in the form of a concentrate.

The following reaction steps, viz. conversion of the resulting bicyclic amide of the formula V' via the mercaptan of the formula II" into the thionitrite of the formula III" and its further conversion, optionally without being isolated from the reaction mixture, into the end product of the formula

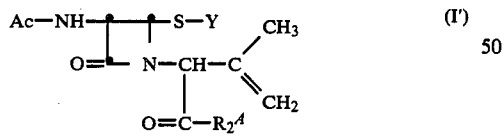
(I')

is carried out in the same manner as described under processes (a) and (b).

In an especially preferred form of the process according to the invention, the starting material used is, for example, a solution of a penicillin-1-oxide of the formula VI in a chlorohydrocarbon, for example ethylene chloride; this starting material is reacted with a compound of trivalent phosphorus and a dehydrating agent, for example with trimethyl phosphite and with a molecular sieve, the dehydrating agent is filtered off, the resulting bicyclic amide of the formula V' is hydrolysed, optionally after previous concentration of the solution, with a dilute mineral acid, for example hydrochloric acid, or sulphonic acid, for example p-toluenesulphonic acid, and the resulting azetidinone II" is reacted, without being isolated from the reaction mixture, with 2 molar equivalents of a nitrosating agent, for example isoamyl nitrite, in the presence of a mercaptan of the formula IVa or of a sulphinic acid of the formula IVb, the thionitrite III" formed as an intermediate further reacting in situ to form the end products of the formula I'.

The process also includes those forms according to which intermediates are isolated and the remaining process steps are carried out with these, the starting materials are manufactured in situ and are used without being isolated or the process is broken off at any stage; furthermore, starting materials can be used in the form of derivatives or formed during the reaction.

The starting materials used and the reaction conditions chosen are preferably such that the compounds indicated at the beginning as being especially preferred are obtained.

The end products of the formula I can be converted into antibiotically active 7β-acylamino-3-cephem-4-carboxylic acids, for example in a manner analogous to that described in German Offenlegungsschrift No. 25 06 330.

The invention relates also to the novel compounds of the formula

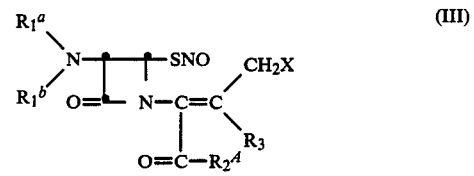
(III)

in which $R_1^a$, $R_1^b$, $R_2^A$, $R_3$ and X have the meanings given under formula I, especially the preferred meanings, and tautomers thereof.

The following Examples serve to illustrate the invention and are not intended to limit it in any way. Temperatures are given in degrees Centigrade.

EXAMPLE 1

3-methyl-2-(4-nitrosothio-2-oxo-3-phenoxyacetaminoazetidin-1-yl)-3-butenoic acid diphenylmethyl ester 0.5 ml of aqueous 40% p-toluenesulphonic acid is added at room temperature to a solution of 516 mg of 3-methyl-2-(4-mercapto-2-oxo-3-phenoxyacetaminoazetidin-1-yl)-3-butenoic acid diphenylmethyl ester in 10 ml of methylene chloride and 15 minutes later 234 mg (2 mmol) of isoamyl nitrite in 2 ml of methylene chloride are added dropwise. After stirring for 7 hours at room temperature, the dark red solution is washed three times with 10 ml of water each time, then concentrated by evaporation with the exclusion of light and degassed in a high vacuum. 3-methyl-2-(4-nitrosothio-2-oxo-3-phenoxyacetaminoazetidin-1-yl)-3-butenoic acid diphenylmethyl ester

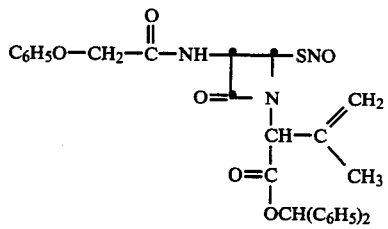

is obtained in the form of a reddish shining foam. Thin layer chromatogram in toluene/ethyl acetate (2:1): $R_f$: 0.7 (olive green spot); IR (in methylene chloride): absorption bands at 1780, 1740, 1695, 1520, 1490 and 1230 cm$^{-1}$.

The starting material can be manufactured as follows:

500 mg (1 mmol) of 3-methyl-2-(3-phenoxymethyl-7-oxo-4-thia-2,6-diazabicyclo[3.2.0]hept-2-en-6-yl)-3-butenoic acid diphenylmethyl ester

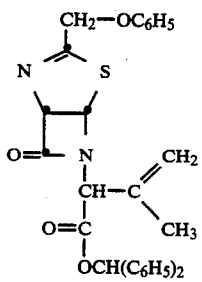

are dissolved in 10 ml of a mixture of methylene chloride/acetone (1:1). 1 ml of 35% perchloric acid is added thereto at room temperature and the clear solution is further stirred at room temperature for 50 minutes. 50 ml of methylene chloride and 50 ml of water are then added, the organic phase is separated off and extraction is carried out twice more with 30 ml of methylene chloride each time. After drying the combined organic phase over sodium sulphate and distilling off the solvent, crystallisation is effected from ether/hexane (1:1). 3-methyl-2-(4-mercapto-2-oxo-3-phenoxyacetaminoazetidin-1-yl)-3-butenoic acid diphenyl methyl ester having a melting point of 54°–57° is obtained.

IR (in methylene chloride): absorption bands at 3400, 3025, 2910, 1775, 1740, 1695, 1515, 1495, 1230, 1175 and 1155 cm$^{-1}$.

$^1$H-NMR (CDCl$_3$, 100 MHz): δ=1.72 (m, 1H), 1.90 (s, 1H), 4.58 (s, 2H), 4.90–5.00 (m, 2H), 4.05–4.15 (m, 2H), 5.40–5.55 (m, 1H) ppm.

EXAMPLE 2

3-methyl-2-[4-(4-methylphenylsulphonylthio)-2-oxo-3-phenoxyacetaminoazetidin-1-yl]-3-butenoic acid diphenylmethyl ester (a) 1.25 g of 4-toluenesulphinic acid and 0.5 g of 40% 4-toluenesulphonic acid are added at room temperature to a solution of 3.0 g of 3-methyl-2-(3-phenoxymethyl-7-oxo-4-thia-2,6-diazabicyclo[3.2.0]hept-2-en-6-yl)-3-butenoic acid diphenylmethyl ester in 30 ml of methylene chloride. After stirring for 15 minutes at room temperature, a solution of 1.87 g of isoamyl nitrite in 10 ml of methylene chloride is added dropwise in the course of 30 minutes. The solution changes colour from yellow to dark red via green and orange. It is stirred for a further 16 hours at room temperature after which the solution has changed again to a yellow-green. The solution is washed three times with saturated bicarbonate solution, the solvent and excess isoamyl nitrite, and also isoamyl alcohol formed, are distilled off in vacuo or in a high vacuum and the resulting 3-methyl-2-[4-(4-methylphenylsulphonylthio)-2-oxo-3-phenoxyacetaminoazetidin-1-yl]-3-butenoic acid diphenylmethyl ester

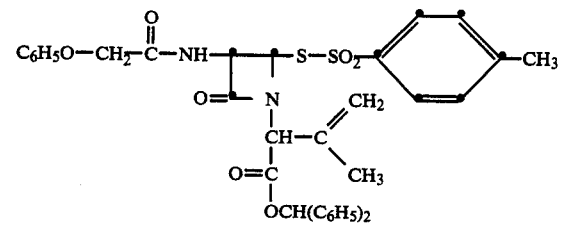

is precipitated with diethyl ether after being dissolved in a little methylene chloride.

$R_f$ in toluene/ethyl acetate (2:1): 0.55; IR (in chloroform): absorption bands at 1782, 1740, 1695, 1340 and 1150 cm$^{-1}$. The same compound can also be obtained in the following manner:

(b) To a solution of 3.82 g (7 mmol) of 3-methyl-2-(4-mercapto-2-oxo-3-phenoxyacetaminoazetidin-1-yl)-3-butenoic acid diphenylmethyl ester in 10 ml of methylene chloride there are added dropwise in the course of 15 minutes 1.56 g (10 mmol) of p-toluenesulphinic acid in 20 ml of methylene chloride followed by 890 mg (10 mmol) of isopropyl nitrite in 5 ml of methylene chloride. After stirring for 15 hours at room temperature with the exclusion of light, the solution, which was originally red, has changed to a pale yellow. The reaction mixture is worked up in the same manner as described under (a).

(c) 5.32 g (10 mmol) of 6-phenoxyacetaminopenicillanic acid diphenylmethyl ester 1-oxide are dissolved in 50 ml of ethylene chloride, 5 g of molecular sieve and 1.85 g of trimethyl phosphite are added at room temperature and the mixture is refluxed for 24 hours. It is then filtered, washed three times with 25 ml of water each time, and concentrated to 35 ml by evaporation in vacuo. 2.1 g (13.5 mmol) of p-toluenesulphinic acid and 1 ml of 30% aqueous p-toluenesulphonic acid are added to the resulting solution of 3-methyl-2-(3-phenoxymethyl-7-oxo-4-thia-2,6-diazabicyclo[3.2.0]hept-2-en-6-yl)-3-butenoic acid diphenylmethyl ester and the whole is stirred at room temperature. A solution of 3.04 g (26 mmol) of isoamyl nitrite in 5 ml of ethylene chloride is then added dropwise in the course of 15 minutes, the internal temperature rising from 22° to 27°. The solution changes colour via pale and dark green to dark red. The solution is stirred for a further 18 hours at room temperature with the exclusion of light, after which the colour of the solution has changed back to yellow again. Working up is carried out in the same manner as described under (a).

EXAMPLE 3

2-[4-(benzthiazol-2-yldithio)-2-oxo-3-phenoxyacetaminoazetidin-1-yl]-3-methyl-3-butenoic acid diphenylmethyl ester 400 mg of 40% aqueous p-toluenesulphonic acid and 1.55 g (17 mmol) of isopropyl nitrite are added to a solution of 4.0 g (8 mmol) of 3-methyl-2-(3-phenoxymethyl-7-oxo-4-thia-2,6-diazabicyclo[3.2.0]hept-2-en-6-yl)-3-butenoic acid diphenylmethyl ester in 12 ml of methylene chloride and the solution is stirred for 6 hours at room temperature with the exclusion of light. A solution of 1.67 g (10 mmol) of 2-mercaptobenzthiazole in 30 ml of ethyl acetate is then added dropwise in the course of 30 minutes and the whole is stirred for a further 12 hours at room temperature. After this period, the thin layer chromatogram indicates almost complete conversion to the title compound. Working up is carried out in a manner analogous to that described in Example 2 (a). The title compound has a melting point of 140°–141°.

EXAMPLE 4

3-methyl-2-(4-nitrosothio-2-oxo-3-phenylacetaminoazetidin-1-yl)-3-butenoic acid diphenylmethyl ester In a manner analogous to that described in Example 1, the title compound is obtained in the form of a reddish oil using 3-methyl-2-(4-mercapto-2-oxo-3-phenylacetaminoazetidin-1-yl)-3-butenoic acid diphenylmethyl ester as the starting material; thin layer chromatogram in toluene/ethyl acetate (2:1): $R_f$ 0.45.

The starting material can be manufactured in a manner analogous to that described in Example 2(c): 6-phenylacetaminopenicillanic acid diphenylmethyl ester 1-oxide is reacted with trimethyl phosphite and a molecular sieve in ethylene chloride and the resulting 2-(3-benzyl-7-oxo-4-thia-2,6-diazabicyclo[3.2.0]hept-2-en-6-yl)-3-methyl-3-butenoic acid diphenylmethyl ester is hydrolysed with aqueous p-toluenesulphonic acid.

EXAMPLE 5

The following compounds can be manufactured in a manner analogous to that described in Example 2(c). 3-methyl-2-[4-(4-methylphenylsulphonylthio)-2-oxo-3-phenylacetaminoazetidin-1-yl]-3-butenoic acid diphenylmethyl ester, m.p. 75°, thin layer chromatogram in toluene/ethyl acetate (1:1): $R_f$ 0.47, and 2-[4-(benzthiazol-2-yldithio)-2-oxo-3-phenylacetaminoazetidin-1-yl]-3-methyl-3-butenoic acid diphenylmethyl ester, m.p. 134°–136°, thin layer chromatogram in toluene/ethyl acetate (1:1): $R_f$ 0.52.

I claim:

1. Process for the manufacture of 4-thioazetidinone compounds of the formula

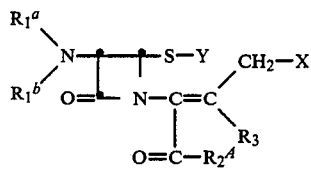
(I)

in which $R_1{}^a$ represents an acyl group Ac of the formula

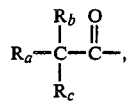
(IA)

in which (1) $R_a$ represents phenyl that is unsubstituted or substituted by hydroxy, protected hydroxy, lower alkyl, lower alkoxy, lower alkanoyloxy, benzoyloxy, halogen, lower alkylsulphonylamino, nitro or aminomethyl that is unsubstituted or substituted by lower alkyl and that is optionally protected; or thienyl, furyl, cyclohexadienyl or cyclohexenyl each of which is substituted by lower alkyl or aminomethyl that is unsubstituted or substituted by lower alkyl and that is optionally protected; or thiazolyl substituted by di-lower alkylamino or protected amino; $R_b$ represents hydrogen and $R_c$ represents hydrogen, hydroxy, protected hydroxy, protected amino, carboxyl or sulpho; or in which (2) $R_a$ represents protected 3-amino-3-carboxypropyl; cyano; 1-tetrazolyl; phenoxy that is unsubstituted or substituted by hydroxy, protected hydroxy, lower alkyl, lower alkoxy, lower alkanoyloxy, benzoyloxy, halogen, lower alkylsulphonylamino, nitro or aminomethyl that is unsubstituted or substituted by lower alkyl and that is optionally protected; or pyridylthio, and $R_b$ and $R_c$ represent hydrogen, or in which (3) $R_a$ represents phenyl that is unsubstituted or substituted by hydroxy, protected hydroxy, lower alkyl, lower alkoxy, lower alkanoyloxy, benzoyloxy, halogen, lower alkylsulphonylamino, nitro or by aminomethyl that is unsubstituted or substituted by lower alkyl and that is optionally protected; or thienyl or furyl each of which is substituted by lower alkyl or aminomethyl that is unsubstituted or substituted by lower alkyl and that is optionally protected; or thiazolyl substituted by di-lower alkylamino or protected amino; and $R_b$ and $R_c$ together represent syn-lower alkoxyimino; and $R_1{}^b$ represents hydrogen; $R_2{}^A$ represents lower alkoxy; 2-halo-lower alkoxy; 2-lower alkylsulphonyl-lower alkoxy; 2-lower alkenyloxy; methoxy mono- or di-substituted by phenyl that is optionally substituted by lower alkoxy and/or nitro; trityloxy; or phenoxy that is optionally substituted by nitro or halogen; $R_3$ is methyl, hydroxy, lower alkoxy, phenyl-lower alkoxy, lower alkanoyloxy, sulphonyloxy, nitrito, phosphinoyloxy, phosphoryloxy, halogen, cyano, nitro, or amino that is di-substituted by lower alkyl, lower alkoxy-lower alkyl, lower alkylthio-lower alkyl, phenyl and/or cycloalkyl or that has as substituent lower alkylene or lower alkylene that is interrupted by oxygen, sulphur or optionally lower alkylated nitrogen; X represents hydrogen or halogen and Y represents a radical —SR$_4$ or —SO$_2$—R$_5$ is which R$_4$ represents thiadiazolyl, oxathiazolyl, diazolyl, oxazolyl, thiazolyl, benzoxazolyl or benzthiazolyl, each of which is optionally substituted by lower alkyl, and R$_5$ represents lower alkyl, cycloalkyl; or phenyl or naphthyl each of which is unsubstituted or substituted by lower alkyl, lower alkoxy, halogen, phenyl, phenoxy or nitro; or, when R$_3$ represents hydroxy or methyl, isomers thereof represented by the formula

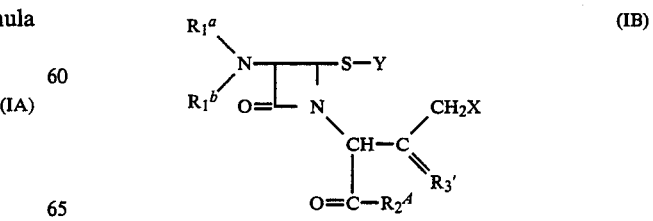
(IB)

wherein $R_3'$ is oxo or methylene, characterised in that a compound of the formula

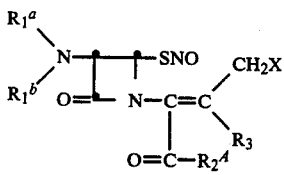
(III)

or, when $R_3$ represents hydroxy or methyl, an isomer thereof represented by the formula IIIB

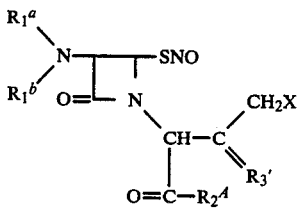
IIIB wherein $R_3'$ represents oxo or methylene is treated with a nitrosating agent and a compound of the formula H-Y (IV).

2. Process according to claim 1, characterised in that compounds of the formula I in which $R_1{}^a$ represents an acyl group Ac of the formula

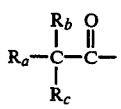
(IA)

in which $R_a$ represents phenyl or phenoxy each of which is unsubstituted or substituted by protected hydroxy, lower alkoxy, or by protected aminoethyl, or thienyl, furyl, cyclohexadienyl, or protected 3-amino-3-carboxypropyl, and $R_b$ and $R_c$ represent hydrogen, $R_1{}^b$ represents hydrogen, $R_2{}^A$ represents lower alkoxy, 2-halo-lower alkoxy, 2-lower alkenyloxy, benzyloxy that is unsubstituted or substituted in the 4-position by nitro; diphenylmethoxy that is unsubstituted or disubstituted in the 4- and 4'-position by methoxy; or trityloxy, $R_3$ represents methyl, lower alkoxy, phenyl-lower alkoxy, hydroxy, sulphonyloxy, nitrito, phosphinoyloxy, phosphoryloxy, halogen, cyano, nitro, di-lower alkylamino, dicycloalkylamino, pyrrolidin-1-yl, morpholin-4-yl or 4-methylpiperazin-1-yl, X represents hydrogen or halogen, and Y represents oxazoloylthio, thiazolylthio, benzoxazol-2-ylthio or benzthiazol-2-yl-thio, or benzenesulphonyl that is unsubstituted or substituted by lower alkyl, lower alkoxy, halogen, or by nitro, or, when $R_3$ represents hydroxy or methyl, isomers thereof represented by the formula (IB) are manufactured.

3. Process according to claim 1 characterised in that compounds of the formula I in which $R_{1a}$ represents an acetyl radical of the formula IA in which $R_a$ represents phenyl, thienyl, or phenoxy, and $R_b$ and $R_c$ represent hydrogen, $R_1{}^b$ represents hydrogen, $R_2{}^A$ represents lower alkoxy, 2-halo-lower alkoxy, benzyloxy optionally substituted in the 4-position by nitro, or diphenylmethoxy, X represents hydrogen or halogen, $R_3$ represents methyl, hydroxy, lower alkoxy, sulphonyloxy, nitrito, di-lower alkylamino, pyrrolidin-1-yl or morpholin-1-yl, and Y represents benzthiazol-2-ylthio, or benzenesulphonyl that is unsubstituted or substituted in the 4-position by lower alkyl or, when $R_3$ represents hydroxy or methyl, isomers thereof represented by the formula (IB) are manufactured.

4. Process according to claim 1, characterised in that 3-methyl-2-[4-(4-methylphenylsulphonylthio)-2-oxo-3-phenoxyacetaminoazetidin-1-yl]-3-butenoic acid diphenylmethyl ester is manufactured.

5. Process according to claim 1, characterised in that 2-[4-(benzthiazol-2-yldithio)-2-oxo-3-phenoxyacetaminoazetidin-1-yl]-3-methyl-3-butenoic acid diphenylmethyl ester is manufactured.

6. Process according to claim 1, characterised in that 3-methyl-2-[4-(4-methylphenylsulphonylthio)-2-oxo-3-phenylacetaminoazetidin-1-yl]-3-butenoic acid diphenylmethyl ester is manufactured.

7. Process according to claim 1, characterised in that 2-[4-(benzthiazol-2-yldithio)-2-oxo-3-phenylacetaminoazetidin-1-yl]-3-methyl-3-butenoic acid diphenylmethyl ester is manufactured.

8. Process according to claim 1 characterised in that the starting compound of the formula III is manufactured in situ by treating a mercaptoazetidinone of the formula

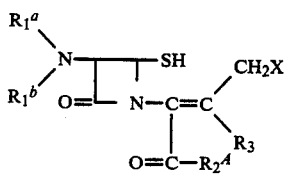
(II)

or an alkali metal salt, alkaline earth metal salt, silver or mercury salt thereof, or when $R_3$ represents hydroxy or methyl, an isomer thereof represented by the formula (IB) with a nitrosating agent, and further reacting without isolation from the reaction mixture, to form the compounds of the formula I.

9. Process according to claim 1 for the manufacture of compounds of the formula I in which $R_1{}^a$, $R_1{}^b$, $R_2{}^A$, $R_3$, X and Y have the meaning given in claim 1 characterised in that the starting compound of the formula III is manufactured in situ by treating a diazabicycloheptene of the formula

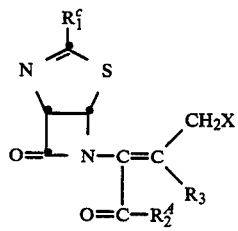
(V)

in which $R_1{}^c$ represents a radical derived from the acyl group of the formula IA but without the carbonyl group, or, when $R_3$ represents hydroxy or methyl, an isomer thereof represented by the formula (IB) with an acidic hydrolysis agent, and treating a resulting intermediate of the formula

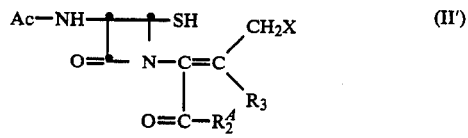
(II')

or when $R_3$ represents hydroxy or methyl, an isomer thereof represented by the formula (IB) optionally without isolation from the reaction mixture, with a nitrosating agent, and further reacting, without isolation from the reaction mixture, to form the compounds of the formula I.

10. Process according to claim 1 for the manufacture of compounds of the formula

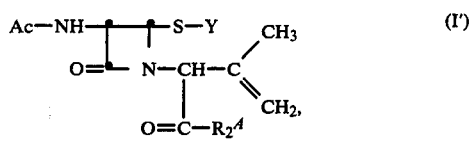

characterised in that the starting compound of the formula

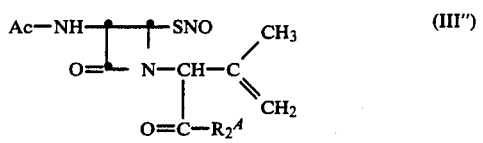

is manufactured in situ by reacting a penicillin-1-oxide of the formula

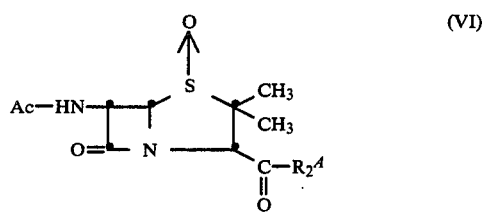

with a tri-lower alkylphosphite or a triarylphosphine, treating a resulting intermediate of the formula

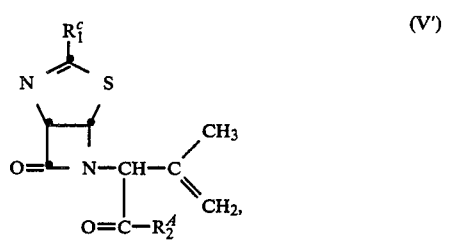

in which $R_1{}^c$ represents a radical derived from the acyl group of the formula IA but without the carbonyl group, optionally without isolation from the reaction mixture, with an acidic condensation agent, and treating the resulting intermediate of the formula

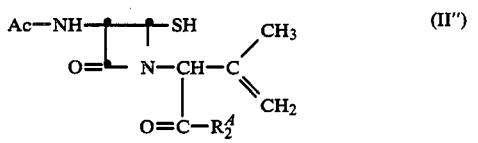

optionally without isolation from the reaction mixture, with a nitrosating agent, and further reacting, without isolation from the reaction mixture, to form the compounds of the formula I.

11. Process according to any one of claims 2–10 and 1, characterised in that a lower alkyl ester of nitrous acid is used as the nitrosating agent.

12. Process according to claim 9 or claim 10, characterised in that an inorganic acid or an organic sulphonic acid is used as the acidic hydrolysis agent.

13. Process according to claim 10, characterised in that a tri-lower alkyl phosphite is used for the production of the intermediate of the formula V'.

14. Process according to any one of claims 2–10 and 1, characterised in that the nitrosation reaction and the reaction with the compounds of the formula IV are carried out in an inert solvent or solvent mixture at from $-70°$ to $+50°$ C.

15. Process according to claim 9 or claim 10, characterised in that the hydrolysis of the diazabicycloheptenes of the formulae V and V' is carried out in water, in an organic solvent or in a solvent mixture at from 10° to 30° C.

16. Process according to claim 10, characterised in that the conversion of the penicillin-1-oxides of the formula VI into the bicyclic amides of the formula V' is carried out in an inert solvent at from 70° to 110° C.

17. Process according to claim 9 or claim 10, characterised in that the reaction steps are carried out without isolating the intermediates obtainable according to the process.

18. Process for the manufacture of 4-nitrosothioazetidinones of the formula

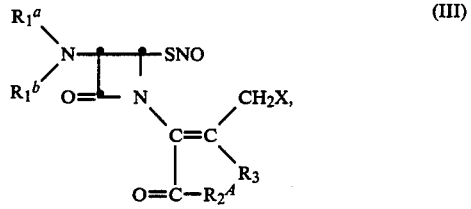

in which $R_1{}^a$ represents an acyl group Ac of the formula

in which (1) $R_a$ represents phenyl that is unsubstituted or substituted by hydroxy, protected hydroxy, lower alkyl, lower alkoxy, lower alkanoyloxy, benzoyloxy, halogen, lower alkylsulphonylamino, nitro or aminomethyl that is unsubstituted or substituted by lower alkyl and that is optionally protected; or thienyl, furyl, cyclohexadienyl or cyclohexenyl each of which is substituted by lower alkyl or aminomethyl that is unsubstituted or substituted by lower alkyl and that is optionally protected; or thiazolyl substituted by di-lower alkylamino or protected amino; $R_b$ represents hydrogen and $R_c$ represents hydrogen, hydroxy, protected hydroxy, protected amino, carboxyl or sulpho; or in which (2) $R_a$ represents protected 3-amino-3-carboxypropyl; cyano; 1-tetrazolyl; phenoxy that is unsubstituted or substituted by hydroxy, protected hydroxy, lower alkyl, lower alkoxy, lower alkanoyloxy, benzoyloxy, halogen, lower alkylsulphonylamino, nitro or aminomethyl that is unsubstituted or substituted by lower alkyl and that is optionally protected; or pyridylthio, and $R_b$ and $R_c$ represent hydrogen, or in which (3) $R_a$ represents phenyl that is unsubstituted or substituted by hydroxy, protected hydroxy, lower alkyl, lower alkoxy, lower alkanoyloxy, benzoyloxy, halogen, lower alkylsulphonylamino, nitro or by aminomethyl that is unsubstituted or substituted by lower alkyl and that is optionally protected; or thienyl or furyl each of which is substituted by lower alkyl or aminomethyl that is unsubstituted or substituted by lower alkyl and that is optionally protected; or thiazolyl substituted by di-lower alkylamino or protected amino; and $R_b$ and $R_c$ together represent syn-lower alkoxyimino; and $R_1{}^b$ represents hydrogen; $R_2{}^A$ represents lower alkoxy; 2-halo-lower alkoxy; 2-lower alkylsulphonyl-lower alkoxy; 2-lower alkenyloxy; methoxy mono- or di-substituted by phenyl that is optionally substituted by lower alkoxy and/or nitro; trityloxy; or phenoxy that is optionally substituted by nitro or halogen, $R_3$ is methyl, hydroxy, lower alkoxy, phenyl-lower alkoxy, lower alkanoyloxy, sulphonyloxy, nitrito, phosphinoyloxy, phosphoryloxy, halogen, cyano, nitro, or amino that is di-substituted by lower alkyl, lower alkoxy-lower alkyl, lower alkylthio-lower alkyl, phenyl and/or cycloalkyl or that has as substituent lower alkylene or lower alkylene that is interrupted by oxygen, sulphur or optionally lower alkylated nitrogen; and X represents hydrogen or halogen, or, when $R_3$ represents hydroxy or methyl, isomers thereof represented by the formula IIIB

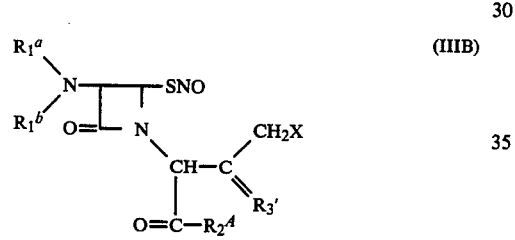

(IIIB)

wherein $R_3'$ is oxo or methylene characterised in that (a) a mercaptoazetidinone of the formula

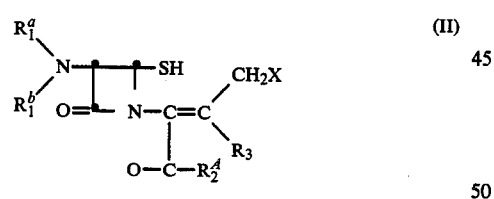

(II)

or an alkali metal salt, alkaline earth metal salt, silver or mercury salt thereof, or, when $R_3$ represents hydroxy or methyl, an isomer thereof represented by the formula

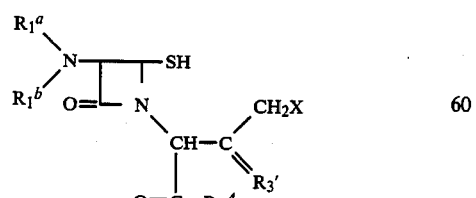

wherein $R_3'$ represents oxo or methylene is treated with a nitrosating agent, or (b) a diazabicycloheptene of the formula

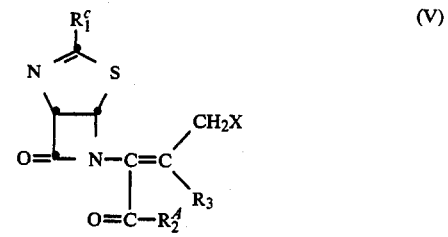

(V)

in which $R_1{}^c$ represents a radical derived from the acyl group of the formula IA but without the carbonyl group, or, when $R_3$ represents hydroxy or methyl, an isomer thereof represented by the formula

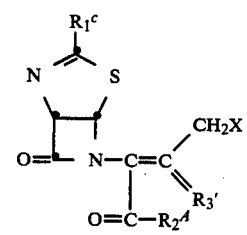

wherein $R_3'$ represents oxo or methylene is treated with an acidic hydrolysis agent and a resulting intermediate of the formula

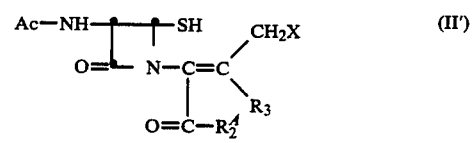

(II')

or, when $R_3$ represents hydroxy or methyl an isomer thereof represented by the formula

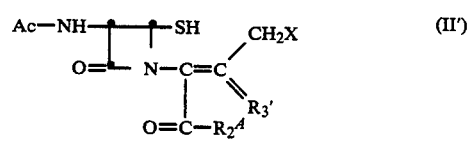

(II'')

wherein $R_3'$ represents oxo or methylene is treated with a nitrosating agent, optionally without being isolated from the reaction mixture, or (c) for the manufacture of 4-nitrosothioazetidinones of the formula

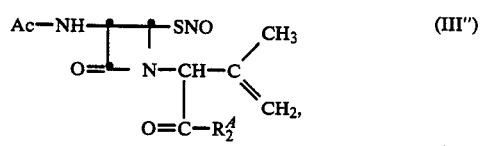

(III'')

a penicillin-1-oxide of the formula

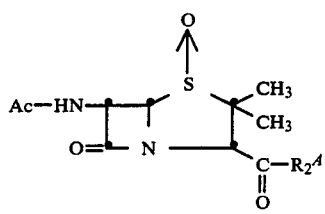

.(VI)

is reacted with a tri-lower alkyl phosphite or a triarylphosphine, a resulting intermediate of the formula

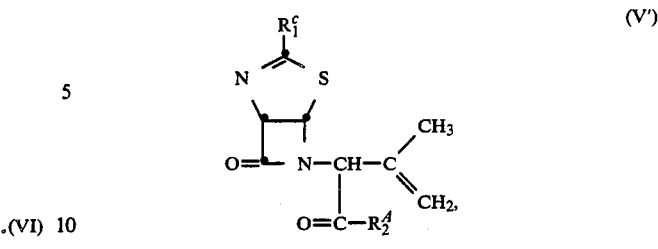

in which $R_1^c$ has the meaning given under formula V, is treated with an acidic condensation agent, optionally without being isolated from the reaction mixture, and the resulting intermediate of the formula

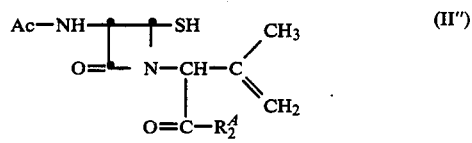

is treated with a nitrosating agent, optionally without being isolated from the reaction mixture.

19. The process of claim 14 wherein said solvent mixture is water/methylene chloride.

20. The process of claim 15 wherein said solvent mixture is water/methylene chloride.

21. The process of claim 16 wherein said inert solvent is ethylene chloride.

* * * * *